(12) United States Patent
Stubbs

(10) Patent No.: US 6,190,391 B1
(45) Date of Patent: Feb. 20, 2001

(54) METHOD OF PREPARING A RESECTED POSTERIOR SURFACE OF A PATELLA TO RECEIVE A PROSTHETIC ELEMENT

(75) Inventor: Bruce T. Stubbs, Ann Arbor, MI (US)

(73) Assignee: Bristol-Myers Squibb Company, New York, NY (US)

( * ) Notice: Under 35 U.S.C. 154(b), the term of this patent shall be extended for 0 days.

(21) Appl. No.: 09/411,737

(22) Filed: Oct. 1, 1999

(51) Int. Cl.$^7$ ................................................. A61B 17/56
(52) U.S. Cl. ............................................................. 606/92
(58) Field of Search ............................... 606/92, 93, 94; 425/470, 469, 457, 2

(56) References Cited

U.S. PATENT DOCUMENTS

| | | | | |
|---|---|---|---|---|
| 32,773 | * | 7/1861 | Kesmodel | 425/2 |
| 277,809 | * | 5/1883 | Taylor | 425/457 |
| 2,554,734 | * | 5/1951 | Gehm | 425/469 |
| 3,242,247 | * | 3/1966 | Watson | 425/470 |
| 3,364,525 | * | 1/1968 | Davy et al. | 425/457 |
| 3,600,752 | * | 8/1971 | Kopp | 425/2 |
| 3,655,306 | * | 4/1972 | Ross et al. | 425/2 |
| 4,593,685 | * | 6/1986 | McKay et al. | 606/92 |
| 4,595,006 | * | 6/1986 | Burke et al. | 606/94 |
| 4,778,473 | | 10/1988 | Matthews et al. . | |
| 4,789,324 | * | 12/1988 | Akhavi | 425/469 |
| 4,888,021 | | 12/1989 | Forte et al. . | |
| 5,197,986 | | 3/1993 | Mikhail . | |
| 5,236,462 | | 8/1993 | Mikhail . | |
| 5,383,937 | | 1/1995 | Mikhail . | |
| 5,522,901 | | 6/1996 | Thomas et al. . | |
| 5,536,271 | | 7/1996 | Daly et al. . | |
| 5,580,353 | | 12/1996 | Mendes et al. . | |
| 5,658,291 | | 8/1997 | Techiera . | |
| 5,705,181 | * | 1/1998 | Cooper et al. | 425/2 |
| 5,723,016 | | 3/1998 | Minns et al. . | |
| 5,965,076 | * | 10/1999 | Banks et al. | 425/2 |
| 6,051,751 | * | 4/2000 | Sioshansi et al. | 623/16 |
| 6,056,526 | * | 5/2000 | Sato | 425/3 |

FOREIGN PATENT DOCUMENTS

7806265  *  12/1978  (NL) ..................................... 425/469

* cited by examiner

Primary Examiner—Nicholas D. Lucchesi
Assistant Examiner—Eduardo C. Robert
(74) Attorney, Agent, or Firm—Todd A. Dawson

(57) ABSTRACT

Apparatus and methods are disclosed for preparing the rejected posterior surface of a patella to receive a prosthetic element. Though applicable to both primary arthroplasty, the invention is ideally suited to revision procedures wherein the patella has previously failed or may be damaged or otherwise compromised. The method includes the steps of applying a layer of material which hardens on the posterior surface of the patella, and urging an inventive die having a planar surface against the layer of material before it hardens so as to create a reconstructed surface which serves as a host for a prosthesis. The preferred hardening material is polymethylmethacrylate (PMMA) due to the widespread use of PMMA as a cement in conjunction with orthopaedic techniques. To provide a thicker build-up, however, the die surface may be recessed relative to a peripheral edge, so that the reconstructed surface is raised relative to the posterior surface of the patella. The reconstructed surface may then be further prepared or used directly as a host for the prosthetic element. Various articles may also be embedded into the hardening material to strengthen the reconstruction or provide attachment mechanisms. As examples, a mesh may be embedded within the material prior to hardening, or one or more cables may be added to engage with tendons attached to the patella.

9 Claims, 3 Drawing Sheets

METHOD OF PREPARING A RESECTED POSTERIOR SURFACE OF A PATELLA TO RECEIVE A PROSTHETIC ELEMENT

FIELD OF THE INVENTION

This invention relates generally to the field of orthopaedics, and to knee-replacement surgical procedures, in particular.

BACKGROUND OF THE INVENTION

In total knee replacement (TKR) surgical procedures, the distal femur and proximal tibia are replaced with prosthetic elements. In conjunction with such procedures, it is also standard practice to replace the posterior portion of the patella. Making reference to FIG. 1, the quadriceps and patellar tendons, 104 and 106, respectively, are twisted to expose the posterior surface of the patella 102, and an oscillating saw is typically employed to resect the bone along a coronal plane more or less flush with the attachments of the tendons 104 and 106. Following this resection, one or more holes are ordinarily drilled into the resected surface to mate with a prosthesis, typically constructed of polyethylene, having posts which mate with the drilled holes. A central hole 108 may be formed, or a plurality of holes such as triangularly spaced-apart holes 110 may be employed, depending upon the fixation arrangement adopted by a given manufacturer.

Making reference to FIG. 2, having performed the appropriate surface preparation, the prosthetic element 202 is affixed to the patella 102 using a suitable adhesive such as polymethylmethacrylate (PMMA). The natural and artificial components are placed into a compressive tool 204 and urged together until the adhesive sets.

Unless the bone of the patella is defective, the technique just described works well for primary arthroplasty in a majority of cases. There are situations, however, wherein the attachment of a prosthetic element to the patella is somewhat more challenging. For example, if the bone is soft or otherwise compromised, the holes bored into the resected surface may not be as stable compared to situations involving healthy, harder bone stock. Problems of this type more commonly arise if, and when, the prosthesis requires revision, which may be performed in conjunction with a revision TKA, independently or if the patellar component itself, becomes loosened or damaged.

Although there are a wide variety of protocols associated with primary patella replacement, the procedures are far less developed when it comes to revision arthroplasty and procedures involving softer bone. Non-primary techniques rely more heavily on the experience of a given surgeon, and less on regimented procedures applicable to a wide variety of situations. Typically, using a revision as an example, the remaining cement must be chipped away and the previously resected surface somehow filed down to create a new host. Either the same holes used in the previous procedure are redrilled, or new ones are formed, but in any case, the result may be less than adequate, resulting in a looser fit of the prosthetic component when installed. According, any methods or apparatus which would improve procedures associated with these more challenging patella replacement surgeries would be welcomed and embraced by the orthopaedic community.

SUMMARY OF THE INVENTION

The subject invention resides in apparatus and methods for preparing the posterior surface of a patella to receive a prosthetic element. Although the invention is suited to revision procedures, wherein the posterior surface has been previously rejected, the invention is likewise applicable to primary techniques, particularly if the patella surface is soft or otherwise defective.

According to a method aspect of the invention, a layer of hardening material is applied to the posterior surface of the patella. Polymethylmethacrylate (PMMA) is the preferred choice due to its widespread use as a cement in conjunction with orthopaedic techniques. A shaped die is provided according to the invention, which is urged against the hardening material to create a reconstructed surface on the posterior surface of a patella. The reconstructed surface may then be further prepared or used directly as a host for the prosthetic element. In terms of further preparing the reconstructed surface, the method of the invention may include the step of forming one or more cavities into the posterior surface of patella prior to applying the layer of material.

The shaped die preferably includes a planar surface where it contacts the hardening material. To provide a thicker build-up, however, the die surface may be recessed relative to a peripheral edge, so that the reconstructed surface is raised relative to the posterior surface of the patella. Various articles may also be embedded into the hardening material to strengthen the reconstruction or provide attachment mechanisms. As examples, a mesh may be embedded within the material prior to hardening, or one or more cables may be added to engage with tendons attached to the patella.

DETAILED DESCRIPTION OF THE INVENTION

Figure 1:
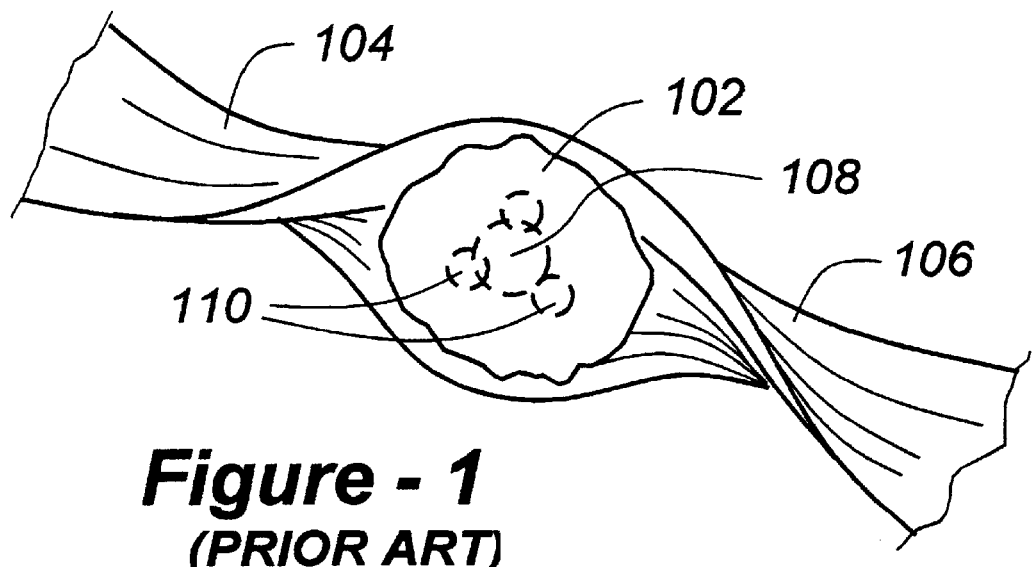
FIG. 1 is a drawing of the posterior surface of a human patella having been resected to receive a prosthetic component.
Figure 2:
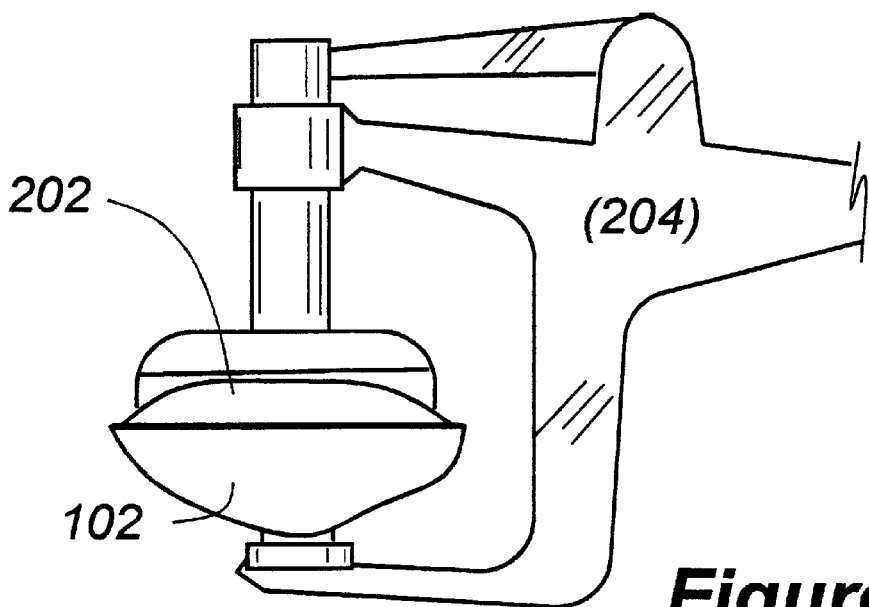
FIG. 2 is a side-view illustration of a prior-art clamp of the type used to affix a prosthetic component to a resected natural patella.
Figure 3:
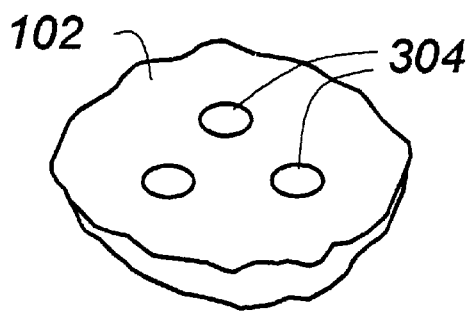
FIG. 3 is a drawing which shows the way in which a plurality of holes are formed into patellar bone to cooperate with a corresponding implant having a plurality of posts.

Having previously discussed the prior-art apparatus and methods of FIGS. 1 and 2, the reader's attention is directed to FIG. 3, which illustrates a patella component 102 having removed a previously installed primary prosthesis (not shown). Typically, the orthopaedic surgeon flips the patella around, as shown in FIG. 1, then, using an osteotome or other cutting tool, removes the previously implanted component at the interface of the resection, using chipping and/or prying actions. This leaves a surface which is less than optimal to work with, including a non-smooth surface overall, and with the cavities 304 perhaps including parts of the posts from the previously installed prosthesis.

Figure 4:
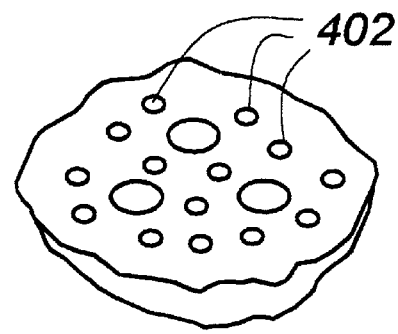
FIG. 4 is a drawing which shows how additional holes may be formed according to the invention for improved adhesive adherence.

According to the invention, additional holes 402, shown in FIG. 4, are preferably drilled into the posterior surface of the patella in a spaced-apart, perhaps random arrangement. The holes 304 may be redrilled or, particularly if the entire post of the primary prosthesis remains therein, may simply be left in tact. The posterior surface of the patella may be filed if any gross protrusions or irregularities are present.

Figure 5:
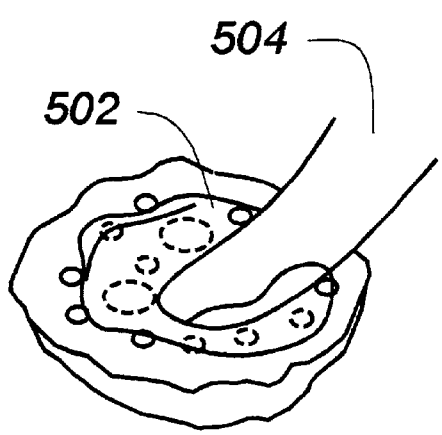
FIG. 5 is a drawing which shows how a finger or tool may be used to apply cement onto the resected surface of a patella according to the invention.

As shown in FIG. 5, a layer of build-up material 502 is applied, either manually, as with an individual's finger 504, or a spatula or other spreading tool may be used. In the preferred embodiment, PMMA is the substance of choice since PMMA is widely used in the orthopaedic profession for prosthesis cementation, and which sets into a hard but workable surface. Preferably the PMMA is allowed to set somewhat so that it has a paste-like consistency. In any case, the material is preferably forced into all of the surface depressions, whether present upon removal of the prosthesis or newly added, but leaving a thin layer of the material for resurfacing. Although this discussion centers on the applicability of the invention to revision techniques, the invention is not limited in this regard, but may also be applied to any primary situation wherein the resected bone might be less than ideal for direct fixation.

Figure 6:
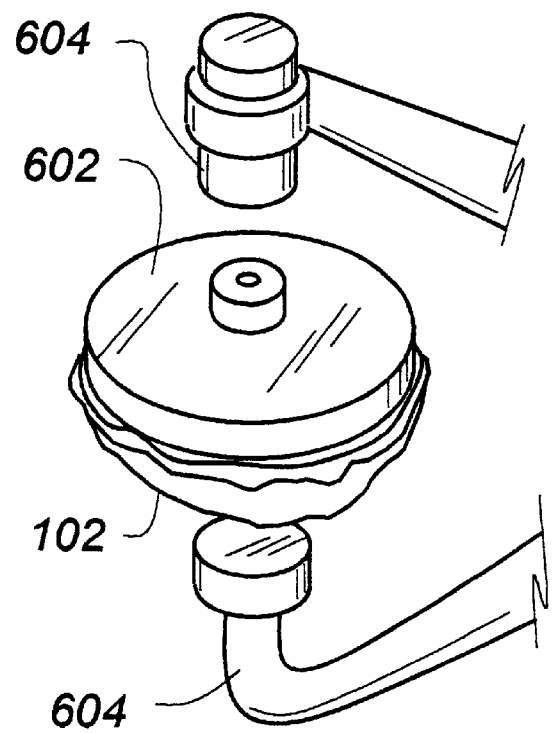
FIG. 6 is a drawing which shows a die according to the invention operative to form a planar surface into a build-up material for surface reconstruction.
Figure 7:
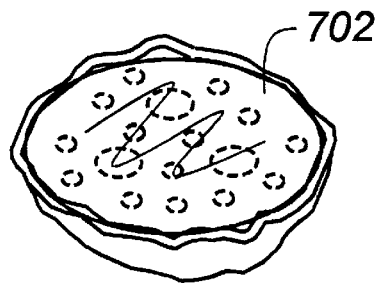
FIG. 7 is a drawing which shows the surface formed according to FIG. 6 as seen from an oblique perspective.

Having applied the layer of hardening material as shown in FIG. 5, a die 602 is provided according to the invention, which is placed onto the material before it hardens, and a clamp device 604 is used to compress the die 602 against the patella 102. Although the die 602 is specially prepared according to the invention, a standard clamp such as that shown in FIG. 2 may be utilized to compress the die 602. Although the surface of the die 602 in contact with the hardening material is not shown in FIG. 6, it is preferably a planar surface, so that the reconstructed surface 702 is again flat, as shown in FIG. 7.

Figure 8:
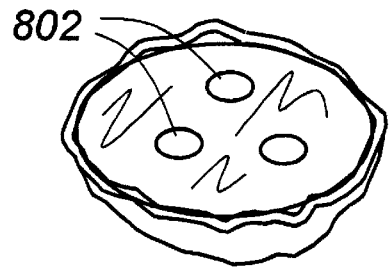
FIG. 8 is a drawing which illustrates the way in which one or more apertures may be formed into an adhesive-bearing surface.

Once the reconstructed surface has been formed according to the techniques just described, additional aperture such as 802 may be formed into the surface as shown in FIG. 8 for alignment with a commercially available prosthesis element. Although multiple holes 802 are shown in FIG. 8, more or fewer may be provided, depending upon the style of implant. The newly formed holes 802 may or may not correspond to holes previously formed in the surface, as shown in FIGS. 1 and 3.

Figure 9:
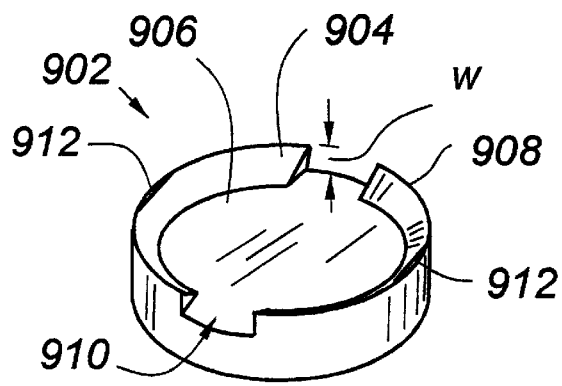
FIG. 9 is a drawing which shows an alternative die according to the invention capable of realizing a thicker build-up of surface reconsideration.
Figure 10:
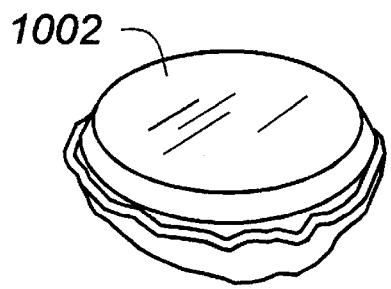
FIG. 10 is a drawing which shows the build-up made possible by the die of FIG. 9.

To provide a thicker build up of material 1002, as shown in FIG. 10, a die depicted generally as 902 in FIG. 9 may be provided having a planar surface 906 which is spaced apart by a thickness W from a peripheral edge 908. Preferably, a die of this type has sloped side walls 904, making it easier to remove, and one or more channels 910 enabling the hardening material to escape during compression. This configuration allows the peripheral edge 908 of the die to seat against the resected bone, so that the reconstructed surface 1002 is planar and parallel to the resection. Small truncations 912 are also preferably provided, so that a tool may be inserted into the slots left by truncations 912, enabling the die 902 may be easily pried off once the material has set.

Figure 11:
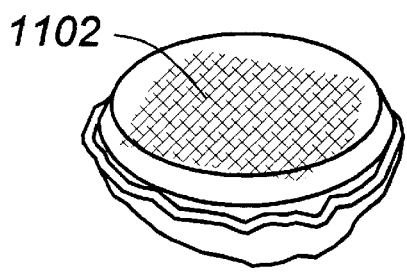
FIG. 11 is a drawing which shows how a mesh or other reinforcement material may be included within a build-up surface according to the invention.
Figure 12:
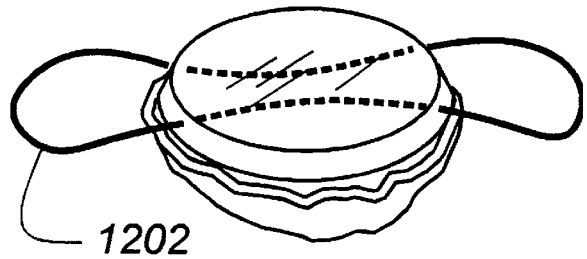
FIG. 12 is a drawing which shows how a cable may be embedded into a reconstructed patellar surface.

To add strength or other useful features, a mesh 1102 may be embedded within the material prior to hardening, as shown in FIG. 11. Preferably, a first layer of material would be applied manually as shown in FIG. 5, the mesh laid down on that material, and a thicker amount of material placed thereover onto which a die such as that shown in FIG. 9 may be used. Alternatively, as shown in FIG. 12, a cable 1202 may be embedded within the hardening material, particularly if the build-up is thicker, for the purpose of engaging with the tendons above and below the patella, or for other purposes. Although a single thicker build up W is shown with respect to FIGS. 9–12, it will be evident to one of skill in the art that different dies may be provided to form different thicknesses of material, and that the diameter of the die, regardless of the thickness, may be changed to suit different sized patellar bones.

I claim:

1. A method of preparing a resected posterior surface of a patella to receive a prosthetic element, comprising the steps of:

applying a layer of material which hardens on the posterior surface of the patella;

providing a die having a die surface; and urging the die surface against the layer of material before it hardens so as to create a reconstructed surface on the posterior surface of a patella.

2. The method of claim 1, further including the step of adhering the prosthetic element to the reconstructed surface.

3. The method of claim 1, wherein the material is PMMA.

4. The method of claim 1, further including the step of forming one or more cavities into the posterior surface of patella prior to applying the layer of material.

5. The method of claim 1, wherein the die surface is planar.

6. The method of claim 1, wherein the die surface is recessed relative to a peripheral edge on the die so that the reconstructed surface is raised relative to the posterior surface of the patella.

7. The method of claim 1, further including the step of embedding a mesh within the material prior to hardening.

8. The method of claim 1, further including the step of embedding one or more cables within the material prior to hardening.

9. The method of claim 8, wherein the cables are adapted to engage with tendons attached to the patella.

* * * * *